United States Patent [19]

Kyllonen et al.

[11] Patent Number: 5,373,841
[45] Date of Patent: Dec. 20, 1994

[54] SELF-OPERATED NASAL HUMIDIFIER

[76] Inventors: David M. Kyllonen, 405 Snowflake Cir., Jeffersonville, Pa. 19403; Charles F. Kyllonen, 2592 Ashurst Rd., University Heights, Ohio 44118

[21] Appl. No.: 830,944

[22] Filed: Feb. 4, 1992

[51] Int. Cl.⁵ .......................................... A61M 15/08
[52] U.S. Cl. ............................. 128/203.18; 128/204.25
[58] Field of Search .................. 128/200.21, 203.18, 128/207.18, 204.25, 201.13, 200.11; 604/94

[56] References Cited

U.S. PATENT DOCUMENTS

| | | | |
|---|---|---|---|
| 429,321 | 6/1890 | Ramey | 128/203.18 |
| 605,436 | 6/1898 | Kellogg | 128/203.18 |
| 3,903,216 | 9/1975 | Allan | 128/200.11 X |
| 4,200,099 | 4/1980 | Guenzel | 128/203.15 |
| 4,240,418 | 12/1980 | Rosskamp | 128/203.15 |
| 4,570,630 | 2/1986 | Elliott | 128/203.15 |
| 4,819,625 | 4/1989 | Howe | 128/200.18 |
| 4,829,997 | 5/1989 | Douwens | 128/201.13 |
| 4,905,688 | 3/1990 | Vicenzi | 128/204.21 |
| 5,054,478 | 10/1991 | Grychowski | 128/200.21 |

FOREIGN PATENT DOCUMENTS

| | | | |
|---|---|---|---|
| 867142 | 7/1949 | Germany | 128/204.25 |
| 188 | of 1899 | United Kingdom | 128/203.18 |
| 992069 | 1/1983 | U.S.S.R. | 128/200.21 |

*Primary Examiner*—Edgar S. Burr
*Assistant Examiner*—Eric P. Raciti
*Attorney, Agent, or Firm*—Eugene E. Renz, Jr.

[57] ABSTRACT

A self-operated nasal humidifier comprising a container adapted to hold liquid heated and a lid detachably secured to the container by means of cooperating threads or other means. The lid houses a venturi and air passage means between the venturi and the lid bottom. The venturi has at its opposite ends inlet and outlet means detachably secured to air receiving and evacuation conduits, respectively. The means for delivering heated humidified air to the nasal cavity involves exhalation by the user into the receiving conduit and through the venturi where vapor above the heated liquid mixes with the exhaled air stream for issue at a controlled temperature.

8 Claims, 1 Drawing Sheet

SELF-OPERATED NASAL HUMIDIFIER

FIELD OF THE INVENTION

The present invention relates to an apparatus for medical treatment generally, and for treatment of ailments associated with the nasal mucosa, in particular. The principal object of the invention is to provide a new and self-operated device for the therapeutic treatment of nasal congestion and dehydration which is self-operated. The means for delivering a stream of heated humidified air to the nasal cavity involves exhalation by the patient into the apparatus providing an air/liquid vapor mixture which, in turn, issues to the patient at a controlled temperature.

A further object of the present invention is to provide a nasal humidifier that is simple in design, manufacture and use, and that requires no bulky or intricate heating mechanisms.

Still another object of the present invention is to provide an affordable means of therapeutic treatment suitable for home use.

BACKGROUND OF THE INVENTION

Various forms of apparatus are known for supplying heated and humidified air to patient for inhalation therapy. Examples of such apparatus are described in U.S. Pat. No. 2,449,853 to Karp, U.S. Pat. No. 3,526,226 to Stem, and U.S. Pat. No. 4,635,630 to Noir et al.

The prior an apparatuses mentioned hereinabove are generally intended to supply air only for inhalation purposes in response to a breathing-in action by a patient and are not designed to provide a flow of warm humidified air to the nasal mucosa. In none of the prior art apparatus is there a teaching or suggestion that the stream of vapor reaches the nasal mucosa of the patient without requiring inhalation by the patient.

Applicant is aware of U.S. Pat. Nos. 4,369,777 and 4,401,114 to Lwoff et al., in which a stream of heated and humidified air is supplied to the nasal mucosa, but said inventions do not provide humidified air by active participation of the patient in the form of exhalation. Furthermore, the former of the two Lwoff et al. apparatuses is not hand-held, but is instead awkward and cumbersome comprising a heating and combining apparatus located in an outlet member which is remotely connected to the remainder of the apparatus via an air conduit and water conduit. Both Lwoff et al. apparatuses are complex in design and significantly more expensive than the present invention.

Applicant is also aware of the teachings of U.S. Pat. No. 4,523,589 to Krauser which houses a fan or blower and temperature control heating elements to warm the air. Here again, the prior art does not show the user of the device orally providing the air pressure which ultimately forces the air/water vapor mixture into the nasal passages. The Krauser apparatus is also complex in design and expensive relative to the present invention.

Some effort has been directed in the art toward achieving a portable, lightweight and inexpensive gas humidifier as exemplified by U.S. Pat. No. 4,597,917 to Lunsford. However, this device does not provide for repeated or extended therapy as it relies on heat producing chemical substances which, once reacted, are no longer useful. The unit is intended to be disposable and primarily for emergency use only.

SUMMARY OF THE INVENTION

The present invention provides a self-operated nasal humidifier for the treatment of nasal congestion and dehydration. There is thus provided in accordance with an embodiment of the present invention an apparatus comprising a container adapted to hold hot liquid, usually water, and a lid housing a venturi and air passage means between the venturi and the lid bottom. The venturi has at its opposite ends inlet and outlet means connected to air receiving and evacuation conduits, respectively. The means for delivering a stream of heated humidified air to the nasal cavity involves exhalation by the patient into the receiving conduit and through the venturi where vapor above the heated liquid mixes with the exhaled air stream for issue via evacuation conduit at a controlled temperature.

In accordance with a preferred embodiment of the present invention, the outlet temperature of the heated humidified air is safe to the user and is governed by the ratio of primary air exhaled by the user to secondary vapor produced from the heated liquid.

Further in accordance with an embodiment of the present invention, the user is provided with an apparatus simple in design and use which does not involve any moving parts. It does not contain any internal, external or remotely attached heating or power sources and is cost efficient.

BRIEF DESCRIPTION OF THE DRAWINGS

The present invention will be more fully understood and appreciated from the following detailed description taken in conjunction with the drawing where.

DETAILED DESCRIPTION OF THE PREFERRED EMBODIMENT

Figure 1:
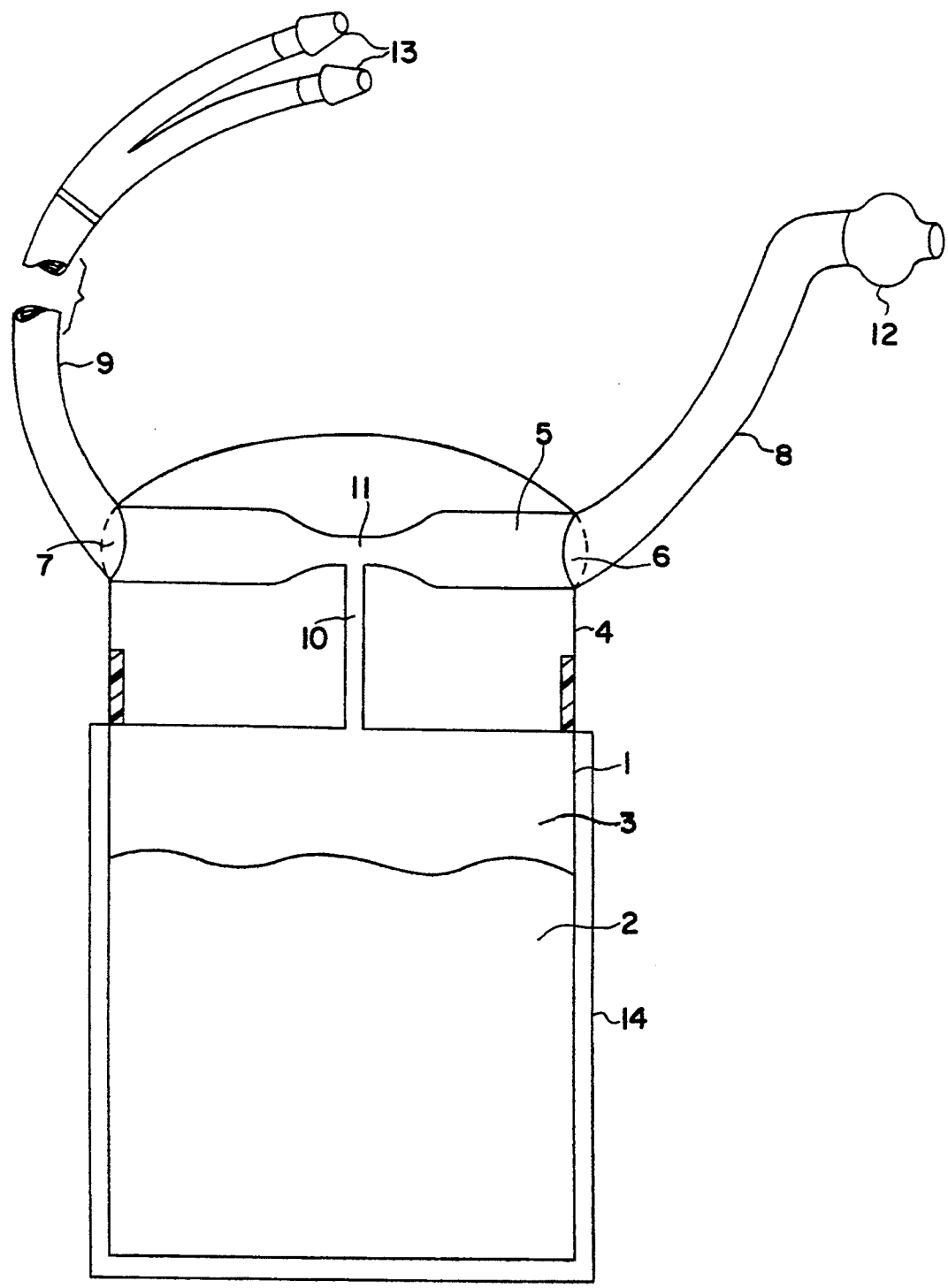
FIG. 1 is a schematic illustration of the present invention constructed and operative in accordance with an embodiment of the present invention.

Referring now to FIG. 1 there is seen a schematic of an apparatus for providing a stream of heated, humidified and sometimes medicated air to the nasal cavity of the user comprising a container 1 adapted to hold hot liquid 2 in reservoir 3 and a lid 4 detachably secured to the container 1 by means of cooperating threads or other means. Container 1 and lid 4 may be made of any suitable material, but preferably of heat resistant plastics that are microwave and dishwasher safe.

A venturi 5 passes horizontally through the axis of rotation of lid 4 and communicates with the atmosphere at its opposite ends forming inlet 6 and outlet 7. Inlet means 6 and outlet means 7 are detachably secured to air receiving conduit 8 and air evacuation conduit 9, respectively.

An air passage means 10 is incorporated into lid 4 and runs axially through its base and extends into venturi 5 at its point of constriction 11 to allow communication between venturi 5 and reservoir 3. In accordance with an embodiment of the invention, conduit means 8 and 9 are formed of a flexible plastic or rubber tubing and are detachable to accommodate cleaning of the apparatus and terminate in oral and nasal adapters 12 and 13, respectively, the latter of which is shown bifurcated to associate with both of the user's nostrils. Adapter 13 may be provided with a single outlet for use in those circumstances where it is desired to treat only one nostril.

The simplicity in design of this apparatus results in a single motive component consisting of a heated humidified gas under pressure. A positive pressure exists above liquid body 2 upon heating and a negative pressure or vacuum exists in venturi 5 beyond its point of constriction 11 upon exhalation by the user into air conduit 8. The ratio of primary air exhaled by the user to secondary vapor emanating from the heated liquid is such that a safe temperature level of the heated humidified therapeutic gas is achieved and issued via evacuation conduit 9 through nasal adapter 13 into the user's nasal passages.

The manner in which the self-operated nasal humidifier is operated is as follows. Heated liquid 2 is poured into reservoir 3 to a fill level marked on the inner wall of container 1. In the alternative, container 1 filled with cool liquid may be heated by conventional means, e.g. by placing it into a microwave oven where liquid body 2 is heated to the desired temperature. For many applications, hot tap water may be used. The container may be insulated by insulation 14 which will serve the purposes of maintaining the temperature of the liquid 2 and to protect the user's hands when the invention is in use. Medication may be incorporated into the issuing air/liquid vapor mixture by adding medication to liquid body 2. Lid 4 is then threaded onto container 1 or attached by other means.

The means for delivering a stream of heated humidified air to the nasal cavity involves exhalation by the patient into air receiving conduit 8 via oral adapter 12. The exhaled air passes through venturi 5 resulting in a negative pressure in venturi 5 and above air passage means 10. This negative pressure, in combination with the positive pressure above liquid body 2 causes vapor to pass through passageway 10 and into venturi 5 where it combines with the exhaled air to form an air vapor mixture at a controlled temperature. The warm, moist air is finally issued into the patient's nasal cavity via evacuation conduit 9 and nasal adapter 13, respectively. The method does not require inhalation of the mixture by the patient as it is delivered under pressure.

In accordance with a preferred embodiment of the present invention, the temperature of the air/liquid vapor mixture upon issue is approximately 43° Centigrade. Said temperature may be, in a variant of the present invention, measured by a thermometer or other device arranged so as to be easily visible to the user.

Generally, it will be understood that the invention may be embodied otherwise than as herein specifically illustrated or described, and that in the illustrated embodiment certain changes in the details of construction and in the form and arrangement of parts may be made without departing from the underlying idea or principles of this invention within the scope of the appended claims.

What is claimed is:

1. A self-operated nasal humidifier for the user controlled delivery of heated humidified gas to the nasal cavity, which humidifier comprises:
   a. a container component comprising, a reservoir adapted to contain a quantity of liquid and associated vapors of the liquid;
   b. a closure component comprising a lid adapted to provide closure of said container component, and wherein said closure component further includes:
      (i) a gas inlet means secured to a gas receiving conduit, said gas receiving conduit terminating in an oral adapter, permitting the gas employed to be air exhaled by a user;
      (ii) a gas passage means communicating with said gas inlet and further comprising a venturi communicating only with a vapor space above the liquid, permitting the air exhaled by the user to be humidified by the vapor of the liquid contained within said reservoir; and
      (iii) a gas outlet means secured to a gas evacuation conduit terminating in a nasal adapter which delivers the humidified air to a nostril of the user.

2. The humidifier of claim 1 wherein said container component and said lid component are detachable.

3. The humidifier of claim 1 wherein said gas receiving and evacuation conduits are formed of a flexible plastic or rubber tubing.

4. The humidifier of claim 3 wherein said gas receiving and evacuation conduits are detachable.

5. The humidifier of claim 1 wherein at least a portion of the container component is comprised of heat resistant, insulative materials.

6. The humidifier of claim 1 further comprising air exhaled by a user, which enters the humidifier through said gas receiving conduit and gas inlet, is humidified by the liquid in said reservoir in passing over said venturi in said gas passage means, and evacuated into the nasal cavity of a user through the gas outlet, said gas evacuation means and nasal adapters, and represents the sole moving part of the humidifier in operation.

7. A self-operated nasal humidifier for the user controlled delivery of heated humidified gas to the nasal cavity, which humidifier comprises:
   a. a container component comprising a reservoir adapted to contain a quantity of liquid and associated vapors of the liquid:
   b. a closure component comprising a lid adapted to provide closure of said container component, and wherein said closure component further includes:
      (i) a gas inlet means secured to a gas receiving conduit, said gas receiving conduit terminating in an oral adapter, permitting the gas employed to be air exhaled by a user;
      (ii) a gas passage means communicating with said gas inlet and further comprising a venturi communicating with said reservoir, said gas passage means further for permitting the air exhaled by the user to be humidified by the vapor of the liquid contained within said reservoir; and
      (iii) a gas outlet means secured to a gas evacuation conduit terminating in a nasal adapter which delivers the humidified air to a nostril of the user, wherein the gas inlet means, gas passage means and gas outlet means remain at a location remote from the quantity of liquid.

8. A method for the self-controlled delivery of a heated humidified gas into the nasal cavity of a user, which method comprises the steps of:
   providing a self-operated nasal humidifier, which humidifier comprises;
   a. a container component comprising a reservoir adapted to contain a quantity of liquid and associated vapors of the liquid;
   b. a closure component comprising a lid adapted to provide closure of said container component, and wherein said closure component further includes:
      (i) a gas inlet secured to a gas receiving conduit, said gas receiving conduit terminating in an oral adapter, permitting the gas employed to be air exhaled by a user;

(ii) a gas passage means communicating with said gas inlet and further comprising a venturi communicating with said reservoir; and (iii) a gas outlet means secured to a gas evacuation conduit terminating in a nasal adapter which delivers the humidified air to a nostril of the user;

exhaling air by means of said oral adapter into said humidifier for the user-controlled delivery of heated humidified gas to the nasal cavity of a user;

humidifying said air by passing said air through said gas passage means over said venturi and exposing the air to the vapor within the reservoir: and evacuating said heated, humidified air into the nasal cavity or the user through said gas outlet, gas evacuation conduit and nasal adapter.

* * * * *